United States Patent [19]

Davis

[11] 4,324,778
[45] Apr. 13, 1982

[54] PHARMACEUTICAL COMPOSITION CONTAINING PARCETAMOL

[75] Inventor: Adrian F. Davis, Hounslow, England

[73] Assignee: Beecham Group Limited, England

[21] Appl. No.: 116,538

[22] Filed: Jan. 29, 1980

[30] Foreign Application Priority Data

Jan. 31, 1979 [GB] United Kingdom ............... 03420/79

[51] Int. Cl.³ ................. A61U 31/165; A61U 31/365
[52] U.S. Cl. ..................................... 424/10; 424/280; 424/324
[58] Field of Search .......................... 424/280, 324, 10

[56] References Cited

PUBLICATIONS

Chem. Abst., vol. 90–637 W (1979).
Rote Liste, 1967, p. 525.
Unlisted Drugs (1), vol. 13, No. 6, ("Pediacyl") Jun. 1961, p. 60i, (2)(1960), p. 33f, Prefacose, (3), vol. 24, No. 4, Apr. 1972, p. 56d, Efferalgan and (4) vol. 21, No. 10, Oct. 1969, p. 157H, Patmin.
Chem. Abst. Chemical Substance Index A–B, vol. 86, under Acetamide, N-OH phenyl.
Chem. Abst. vol. 67, 52498w.

*Primary Examiner*—Sidney J. Friedman
*Attorney, Agent, or Firm*—Jacobs & Jacobs

[57] ABSTRACT

The acute liver toxicity effects of paracetamol are reduced by co-formulating with ascorbic acid derivatives (ascorbate anion bioprecursors) which produce high liver concentrations of ascorbate anion after oral administration of the co-formulation. A suitable ascorbate anion bioprecursor is ascorbyl 6-palmitate.

10 Claims, No Drawings

PHARMACEUTICAL COMPOSITION CONTAINING PARCETAMOL

This invention relates to pharmaceutical compositions having analgesic and antipyretic activity, and more particularly, to compositions comprising paracetamol and bioprecursors of ascorbic acid.

Paracetamol (p-hydroxyacetanilide) is an analgesic and antipyretic agent which is widely used in prescription and non-prescription medicines, often in combination with other biologically active compounds such as caffeine and acetylsalicylic acid. When administered at the recommended dosage regimen it is believed to be a safe and effective therapeutic agent without significant undesirable side effects. However, if the usual recommended single doses are exceeded, severe and often fatal liver damage can occur. Indeed, suicide by paracetamol poisoning has become a major cause for concern. Moreover, there are indications that chronic dosing even at the recommended levels can result in liver damage.

It is believed that the liver toxicity of paracetamol is due to the covalent binding of a paracetamol metabolite to vital liver cell macromolecules. At the recommended dose levels, the metabolite is effectively removed by biochemical processes, but at excessive dose levels, these biochemical processes become depleted and the excess metabolite exerts its toxic effects.

This invention is based on the discovery that a sufficient concentration of ascorbate anion in the liver can prevent or at least mitigate the toxic effects of excessive paracetamol on the liver (centrilobular hepatic necrosis). Unfortunately, ascorbic acid when administered orally is incapable of producing sufficiently high liver concentrations of ascorbate anion to have this antidote effect. The difficulty lies in the fact that absorption of ascorbate through the gastro-intestinal wall is not linearly related to dose. Progressively higher oral doses of ascorbic acid produce smaller and smaller increases in ascorbate concentration in the liver. The effective maximum concentration of ascorbate, achieved after oral dosing of very large amounts of ascorbic acid is, we have found, lower than that required to act as an antidote to paracetamol liver toxicity. Therefore, the discovery mentioned above is exploited in the present invention by using bioprecursors of ascorbate anion which are well absorbed from the gastro-intestinal tract and produce higher and/or more prolonged ascorbate concentrations in the liver after oral administration than can be achieved after oral administration of mole equivalent amounts of ascorbic acid itself.

Accordingly the present invention provides an analgesic and antipyretic pharmaceutical composition adapted for oral administration which comprises paracetamol and an amount of ascorbate anion bioprecursor sufficient, on oral administration of said composition, to reduce the potential liver toxicity effects of the paracetamol content of said composition, said ascorbate anion bioprecursor being absorbable from the gastro-intestinal tract to produce higher and/or more prolonged ascorbate anion concentrations in the liver after oral administration than can be achieved after oral administration of mole equivalent amounts of ascorbic acid itself.

The phrase "ascorbate anion bioprecursor" as used herein means a compound having a chemical structure different from ascorbic acid which, after oral administration, is converted during and/or after absorption through the gastro-intestinal wall to ascorbate anion. It is envisaged that such ascorbate anion bioprecursors may be derivatives of ascorbic acid (structure I):

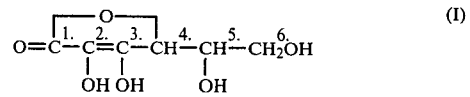

wherein the 2-, 3-, 5- or 6-hydroxy group(s) is (are) chemically modified so as to improve the rate and/or extent of absorption through the gastro-intestinal wall relative to ascorbic acid itself, the chemical modification being such that it is reversed by body enzymes or by other processes during or after passage through the gastro-intestinal wall of produce correspondingly high and/or prolonged liver concentrations of ascorbate anion. Preferred derivatives are those of the general formula:

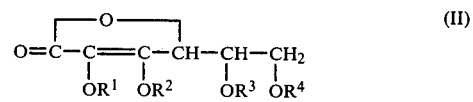

in which $R^1$, $R^2$, $R^3$ and $R^4$, which may be the same or different, are each hydrogen or an alkyl group, preferably long chain alkyl groups having from 10 to 20 C atoms.

The derivatives should be at least sparingly soluble in gastric juices and convertible back to ascorbic acid by chemical or enzymatic processes in vivo.

Particularly preferred R groupings are the "fatty" ester groupings such as the palmitate, stearate or laurylate and in the most preferred compounds, $R^1 = R^2 = R^3 =$ hydrogen while $R^4$ is palmitate, stearate or laurylate.

Other preferred derivatives are cyclic condensation products of the 2,3 or 5,6 hydroxyl groups of ascorbic acid to give isopropylidene or succinate or glutyrate esters. Diesters on the 2,3 position are also useful bioprecursors.

With the exception of the tetraformyl ester, it is believed unlikely that esterification of all four OH groups with non-acid labile ester groupings will produce a bioprecursor with the required good absorption characteristics since such an ester seems likely to be too insoluble in the gastric fluids. However, if the tetra-ester is hydrolysed to some extent in gastric fluids it will have the opportunity to pass through the stomach wall and the hydrolysis equilibrium will ensure absorption of a substantial proportion of the dose.

Bioprecursors in which the 2- and 3-hydroxy groups are free (for example 6-mono esters) may be used in the form of pharmaceutically acceptable salts such as the sodium or potassium salts.

The formation of bioprecursors or "prodrugs" of known pharmacologically active chemical species either to overcome some intrinsic disadvantage such as unpleasant taste or to provide some advantage such as improved bioavailability has been the subject of extensive investigation in recent years. As a result, the literature on prodrugs abounds with examples of chemical modification of, for example hydroxy groups which are reversible by body enzymes or other body processes. An example of this extensive literature is "Prodrugs as Novel Delivery Systems" Ed:Higuchi and Stella; ACS Symposium Series; No. 14 (1975) and "Design of Biopharmaceutical Properties Through Prodrugs and Analogues"; Ed:Roche; American Pharmaceutical Association (1977).

A simple test for the reversibility of the chemical modification embodied by any ascorbate bioprecursor is the rate at which whole blood or tissue homogenate will convert the bioprecursor to ascorbate. This test can easily be performed in vitro according to known procedures.

The liver concentrations of ascorbate following the oral adiministration of a particular bioprecursor may be monitored by analysis of liver samples taken from killed laboratory animals being dosed with the compound. In this way any particular bioprecursor can be evaluated to determine whether it produces higher and/or more prolonged liver concentrations than ascorbic acid itself.

It is believed that the greater the concentration of ascorbate in the liver relative to paracetamol or paracetamol metabolite the greater the protection against liver damage, up to the point, of course, when complete protection is achieved. Some protection appears to be achieved when the concentration of ascorbate:paracetamol in the liver is 1:8 but higher concentrations of ascorbate than this are needed for good or substantially complete protection. Accordingly, in the compositions of this invention it is preferred that the weight ratio of ascorbate bioprecursor:paracetamol should be capable of producing corresponding liver concentrations of at least 1:8, preferably at least 1:4, more preferably at least 1:2 ascorbate:paracetamol. It is envisaged that the theoretical ascorbate anion content of the compositions of the invention will be at least 25% by weight of the paracetamol content and more often will be at least 70%, or even at least 100% of the paracetamol content.

Since the compositions of this invention are intended for oral administration, any of the usual oral dosage forms of pharmaceutical compositions may be adopted. Thus the compositions may be in the form of capsules, tablets or powders for mixing with orally consumable liquids, or liquid syrups. The compositions may include the carriers and excipients conventional in such oral dosage forms. Excipients which may be present include colouring and flavouring materials.

A single dosage unit of the compositions of the present invention will normally contain from 250 mg to 1000 mg of paracetamol, and from 100 to 1000 mg of ascorbic acid equivalent in the ascorbate bioprecursor.

Despite the reduced potential for liver toxicity of compositions of the present invention it is envisaged that they may be offered to the consumer with the contraindications and instructions as to recommended dose conventional in paracetamol formulations.

In another aspect of the present invention there is provided a method of reducing the potential liver toxicity effect of a pharmaceutical composition comprising paracetamol, which method comprises including in said composition an ascorbate anion bioprecursor absorbable from the gastro-intestinal tract, as discussed above.

In another aspect of the present invention there is provided a method of reducing paracetamol induced liver damage which comprises the oral co-administration of paracetamol and ascorbate anion bioprecursor absorbable from the gastro-intestinal tract as discussed above. The paracetamol and ascorbate bioprecursor may be administered together or consecutively.

In another aspect of the present invention there is provided a treatment pack comprising an oral dosage unit comprising paracetamol and an oral dosage unit comprising an ascorbate anion bioprecursor absorbable from the gastro-intestinal tract as discussed above. These two oral dosage units being retained in said pack in association with one another, e.g. by blister packing the two dosage units in the same blister.

The invention is now more fully described with reference to the following Example:

The protective effect of an ascorbate bioprecursor, ascorbyl 6-palmitate, against paracetamol liver toxicity was accessed at several dose levels in groups of twenty mice. It had previously been shown that an oral dose of 450 mg/kg produced moderate liver damage in mice with approximately 35% mortality. In the experiment the assessment of liver damage was by measurement of liver weight increases, which had been shown to be proportional to liver toxicity. The mice were dosed by intubation directly to the stomach.

Results:

TABLE 1

| Group | Treatment | Increase in relative liver weight (gms) |
|---|---|---|
| 20 | Vehicle control | 0 |
| 21 | Paracetamol alone (450 mg/kg) | 1.8 |
| 24 | Paracetamol (450 mg/kg) + 300 mg/kg* Ascorbyl 6-palmitate | 0.6 |
| 25 | Paracetamol (450 mg/kg) + 600 mg/kg* Ascorbyl 6-palmitate | 0.1 |
| 26 | Paracetamol (450 mg/kg) + 900 mg/kg* Ascorbyl 6-palmitate | 0.1 |

These results indicate that ascorbyl palmitate reduces liver toxicity (as measured by increase in liver weight at the dosage tested).

Confirmation of these results was obtained by histopathological methods, as follows:

The liver samples were embedded in paraffin wax; 5 μm sections of each lobe were cut and stained with haematoxylin and eosin. One section from each lobe was examined and scored for the degree of necrosis on the following arbitrary scale.

Score 0 = no necrosis
Score 1 = centrilobular necrosis
Score 2 = centrilobular necrosis and confluent necrosis
Score 3 = confluent necrosis effecting at least 80% of the section For each animal a score was recorded for each lobe and a total score derived from the sum of the four individual lobes. Mean results of 20 animals per group are shown below.

| Group no. | Treatment | Percentage of sections with score | | | | Mean necrosis score |
|---|---|---|---|---|---|---|
| | | 0 | 1 | 2 | 3 | |
| 20 | Vehicle control | 100 | — | — | — | 0 |
| 21 | Paracetamol alone 450 mg/kg | 5 | 24 | 50 | 21 | 7.5 |
| 24 | Paracetamol 450 mg/kg + 300 mg/kg* Ascorbyl 6-palmitate | 28 | 34 | 27 | 11 | 4.75 |
| 25 | Paracetamol 450 mg/kg + 600 mg/kg* Ascorbyl 6-palmitate | 66 | 32 | 2 | 0 | 1.42 |
| 26 | Paracetamol 450 mg/kg + 900 mg/kg* Ascorbyl | 83 | 4 | 5 | 8 | 1.52 |

| Group | | Percentage of sections with score | | | | Mean necrosis score |
|---|---|---|---|---|---|---|
| no. | Treatment | 0 | 1 | 2 | 3 | |
| | 6-palmitate | | | | | |

*These figures represent the weight equivalent of ascorbic acid in the palmitate.

These results clearly show that ascorbyl palmitate reduces paracetamol induced hepatotoxicity.

I claim:

1. An analgesic and antipyretic pharmaceutical composition adapted for oral administration, which comprises paracetamol and an amount of ascorbate anion bioprecursor which ascorbate ion precursor is a derivative of ascorbic acid of the formula (II):

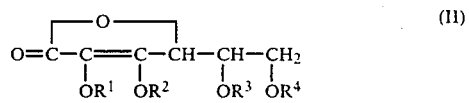

in which $R^1$, $R^2$, $R^3$ and $R^4$, which may be the same or different, are each hydrogen or an alkyl group of 10 to 20 carbon atoms, $R^1$, $R^2$, $R^3$ and $R^4$ not all being hydrogen simultaneously, sufficient, on oral administration of said composition, to reduce the potential liver toxicity effects of the paracetamol content of said composition, said ascorbate anion bioprecursor being absorbable from the gastro-intestinal tract to produce higher and/or more prolonged ascorbate anion concentrations in the liver after oral administration of mole equivalent amounts of ascorbic acid itself, the weight ratio of ascorbate bioprecursor to paracetamol calculated as ascorbic acid equivalents being from 1:4 to 3:1.

2. A composition according to claim 1, characterised in that the ascorbate anion bioprecursor is a derivative of ascorbic acid with the general formula:

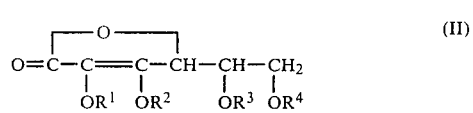

in which $R^1$, $R^2$, $R^3$ and $R^4$, which may be the same or different, are each hydrogen or an alkyl group, with the proviso that $R^1$, $R^2$, $R^3$ and $R^4$ are not simultaneously hydrogen wherein the weight ratio of ascorbate to paracetamol is 1:2.

3. A composition according to claim 1, characterised in that the bioprecursor is ascorbyl 6-palmitate, 6-stearate or 6-laurylate, or a pharmaceutically acceptable salt thereof.

4. A composition according to claim 1, characterised in that the weight ratio of ascorbate anion bioprecursor:paracetamol is capable of producing corresponding liver concentrations of at least 1:8 ascorbate:-paracetamol.

5. A composition according to claim 1, characterised in that the theoretical ascorbate anion content of the composition is from 25 to 100% by weight of the paracetamol content.

6. A composition according to claim 1, in dosage unit form, characterised in that each dosage unit contains from 250 mg to 1,000 mg of paracetamol.

7. A composition according to claim 6, characterised in that each dosage unit contains from 100 to 1000 mg ascorbic acid equivalent in the ascorbate bioprecursor.

8. A treatment pack comprising an oral dosage unit comprising paracetamol and an associated oral dosage unit comprising ascorbate anion bioprecursor as defined in claim 1.

9. A method of reducing paracetamol induced liver damage in humans which comprises administering to the humans a therapeutically active amount of a composition, according to claim 1.

10. A composition according to claim 7, characterised in that each dosage unit contains from 200 to 400 mg ascorbic acid equivalent in the ascorbate bioprecursor.

* * * * *